US006255474B1

(12) United States Patent
Toyomura et al.

(10) Patent No.: US 6,255,474 B1
(45) Date of Patent: Jul. 3, 2001

(54) PROMOTERS FOR SWINE COMPLEMENT INHIBITORS

(75) Inventors: Koji Toyomura; Tatsuya Fujimura; Hiroshi Murakami; Tamotsu Shigehisa, all of Tsukuba (JP)

(73) Assignee: Nippon Meat Packers, Inc., Osaka (JP)

( * ) Notice: Subject to any disclaimer, the term of this patent is extended or adjusted under 35 U.S.C. 154(b) by 0 days.

(21) Appl. No.: 09/180,939
(22) PCT Filed: May 19, 1997
(86) PCT No.: PCT/JP97/01677
  § 371 Date: Nov. 17, 1998
  § 102(e) Date: Nov. 17, 1998
(87) PCT Pub. No.: WO97/44449
  PCT Pub. Date: Nov. 27, 1997

(30) Foreign Application Priority Data

May 17, 1996 (JP) .................................... 8-148335

(51) Int. Cl.$^7$ .................................................. C12N 15/09
(52) U.S. Cl. ........................................ 536/24.1; 435/320.1
(58) Field of Search ................... 435/6, 320.1; 536/23.1, 536/24.1; 530/350

(56) References Cited

FOREIGN PATENT DOCUMENTS

| 9700951 | 1/1997 | (WO) . |
| WO9712035 | 4/1997 | (WO) . |

OTHER PUBLICATIONS

E.R. Oldham, et al., "High–Level Tussue Specific Expression of Human . . . ", *Transplantation Proceedings*, vol. 28, No. 2, Apr. 1996, p. 693.

W. Cui, et al., "Characterization of the Promoter Region . . . ", *The Journal of Immunology*, vol. 151, No. 8, Oct. 15, 1993, pp. 4137–4146.

M. Mora, et al., Protection from complement–mediated injury . . . , *Xenotransplantation*, vol. 3, No. 1, 1996, pp. 63–68.

Robson et al., "Aggregation of human platelets induced by porcine . . . ", Xenotransplantation 3:24–34 (1996).

M. Hosokawa et al., "Molecular Cloning of Guinea Pig Membrane Cofactor Protein", J. Immunology 157:4946–4952 (1996).

K. Toyomura et al., International Immunology, vol. 9, No. 6, pp. 869–876 (1997).

F.H. Bach et al., Transplantation Proceedings, vol. 27, No. 1, pp. 77–79 (Feb. 1995).

K. Toyomura et al., "Expression Cloning and Functional Analysis . . . ", Molecular Immunology, vol. 33, Supplement 1, Jun. 1996, Abstract 38.

A. K. Wintero et al. "Evaluation and characterization of a porcine small intestine cDNA library: analysis of 839 clones" Mammalian Genome. (1996) No. 7, p. 509–517.

F.H. Bach et al. "Xenotransplantation: Endothelial Cell Activation and Beyond" Transplantation Proceedings. (1995) vol. 27, No. 1, p. 77–79.

*Primary Examiner*—James Ketter
(74) *Attorney, Agent, or Firm*—Birch, Stewart, Kolasch & Birch, LLP

(57) ABSTRACT

The present invention provides the base sequence defined as Sequence No. 1, DNA comprising a part of the sequence, or DNA containing the sequence, and relates to a promoter gene of the porcine complement inhibitor. In generating transgenic pigs transformed with human complement inhibitor and/or such thrombosis-inhibiting factors as thrombomudulin (collectively termed the complement inhibitor), DNA of the invention can effectively be used to express the complement inhibitor by integrating the gene into the upstream part of the human complement-inhibitor gene. Since hyperacute rejection, which occurs on transplanting a porcine organ or tissue to man, can be prevented, xenotransplantaion of the porcine organs and tissues to man will become possible. Therefore, the problem of the lack of donors for transplantation can be solved.

3 Claims, 2 Drawing Sheets

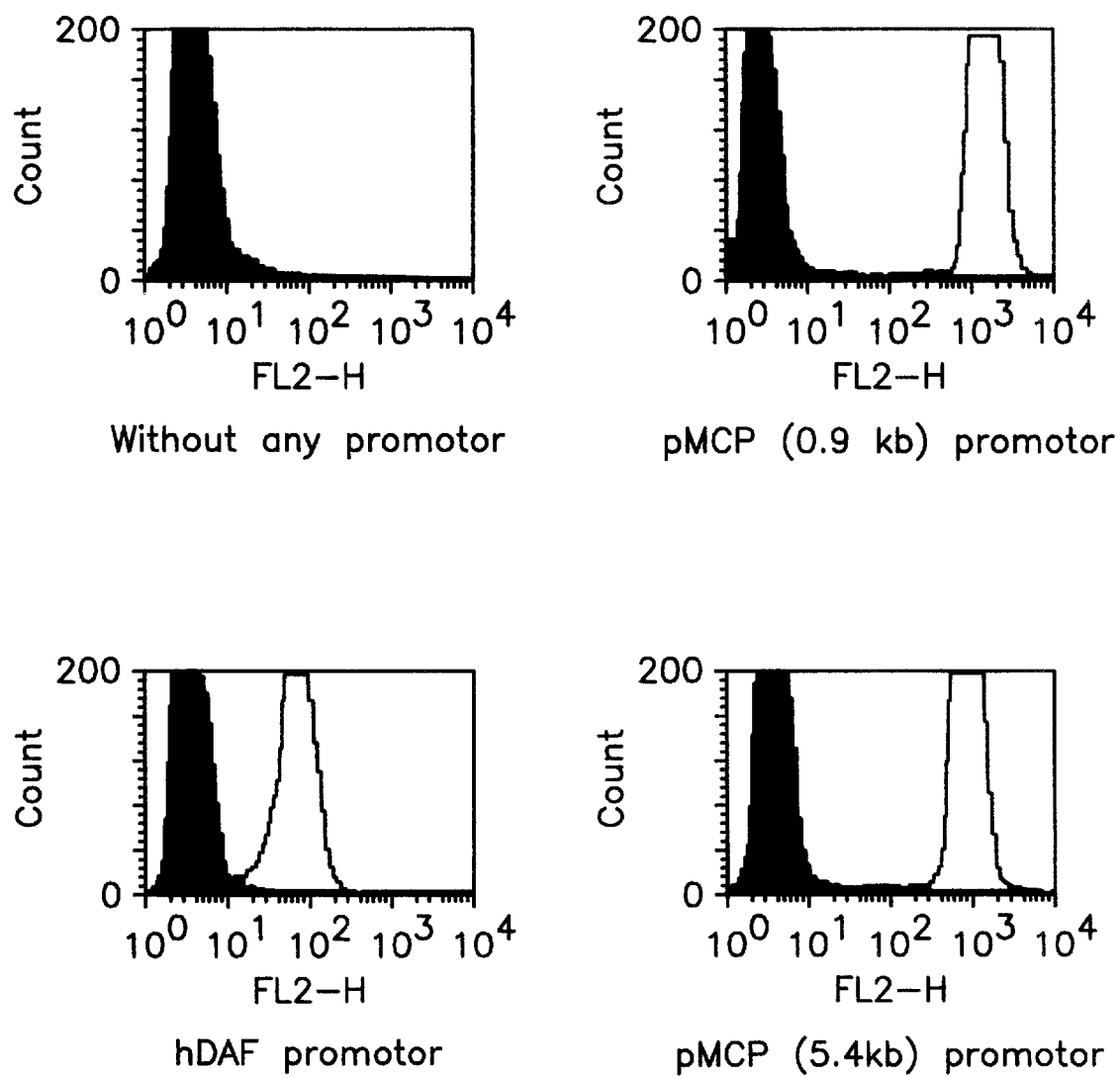

PROMOTERS FOR SWINE COMPLEMENT INHIBITORS

This application is the national phase under 35 U.S.C. §371 of prior PCT International Application No. PCT/JP97/01677 which has an International filing date of May 19, 1997 which designated the United States of America.

TECHNICAL FIELD

This invention provides DNA consisting of a specific base sequence. More particularly, the invention provides a promoter gene for a porcine complement inhibitor.

BACKGROUND OF THE INVENTION

Recently, organ transplantation has widely been carried out in many countries. Development of highly effective immunosuppressants (e.g., Cyclosporin and FK506) has solved the problem of rejection of organs transplanted from man to man, however, lack of donors has become a serious problem. Such a problem has prompted studies on animal-to-man organ transplantation, namely xenotransplantation. Although approximately 3,500 instances of heart transplantation have been performed annually in European countries and the United States, they cover only 20 to 30% of patients who need heart transplantation. Use of animals closely related to human beings as donors (for example, such primates as baboons and chimpanzees) involves a great deal of difficulty due to shortage of these animals and their high intelligence, but use of domestic animals as donors involves less problems. Particularly, pigs have advantages of easy supply due to mass rearing, their organ sizes similar to those of man, and established basic technology including maintenance of the strains. Consequently, organ transplantation from pig to man has been studied.

Of rejections occurring in pig-to-man organ transplantation, acute rejection by major histocompatibility complex (MHC)-related cellular immunity may not occur, since evolutional relatedness between pigs and man is so scarce that there is no similarity between their MHCs. Moreover, application of the effective immunosuppressants may avoid such rejection, if ever occurs.

Human blood, however, contains endogenous antibodies against pigs (namely, natural antibodies). Consequently, if a porcine organ is transplanted to man, the natural antibodies recognize the organ (antigen) resulting in formation of antigen-antibody complexes, which activate human complements. The activated human complements cause necrosis of the transplanted organ (rejection). Such a phenomenon occurs immediately (within an hour) after transplantation, so it is termed hyperacute rejection.

No drug preventing hyperacute rejection caused by complement activation has ever been developed. No human organ is injured by human complements, since factors preventing complement activation are expressed in human organs. Such factors are named complement inhibitors (or complement-inhibiting factors). Of the complement inhibitors, three factors, DAF (decay accelerating factor, CD55), MCP (membrane cofactor protein, CD46) and CD59, are important. It is believed that DAF and MCP inhibit activation of complements by accelerating the destruction of C3b and C3/C5 convertase, and CD59 does so by inhibiting the C9 step.

The complement inhibitors are species specific. Porcine complement inhibitors can inhibit the complement activity of pigs but not that of man. The porcine complement inhibitors cannot inhibit human complements activated by the porcine organ transplanted to man. Therefore, the porcine organ transplanted to man undergoes necrosis.

Pig-to-man organ transplantation triggers not only hyperacute rejection but also thrombin formation and platelet coagulation, resulting in thrombosis in the hosts vascular system as well as the transplanted organ. Components of the blood coagulation pathway, such as thrombin, fibrin and fibrin degradation products may also amplify tissue damage, modify immune responses and augment inflammatory responses (Xenotransplantation, vol. 3(1). 24–34, 1996).

Such problems arising when a porcine organ is transplanted to man will be solved, if human complement inhibitors and/or such thrombosis-inhibiting factors as thrombomodulin (collectively termed as complement inhibitors in the following) are expressed in the porcine organs by genetic engineering. In transplantation of the porcine heart, there will be no problem if the human complement inhibitors are being expressed by porcine vascular endothelial cells.

From such a viewpoint, studies on recombinant pigs (transgenic pigs) integrated with human complement-inhibitor genes have widely been carried out.

It has also been considered to be useful to express such factors that are capable of suppressing thrombosis (e.g., thrombomodulin, Proceedings of the XVth World Congress of the Transplantation Society, pp. 77–79, 1995) with or without the human complement inhibitors in the porcine organs by genetic engineering.

As described above, xenotransplantation by using transgenic pigs integrated with the human complement-inhibitor genes have been studied. Up to the present, promoters derived from the human complement-inhibitor gene or viruses have been used to prepare such transgenic pigs. For the complement inhibitors to be expressed in pigs, however, the promoters originating from pigs may be more efficient. To obtain such promoters, cDNA of the porcine complement inhibitors is needed. Therefore, the present inventors carried out studies to isolate and purify cDNA encoding a porcine complement inhibitor (termed pMCP in the following) and succeeded in isolating and sequencing its cDNA (see Japanese Pat. Appln. No. 178254/1995).

The present inventors further studied and succeeded in identifying and sequencing the promoter region of PMCP by preparing porcine genomic libraries and then screening them with pMCP's cDNA as a probe.

As described above, pMCP's promoter of the invention was derived from pMCP's genomic DNA, which was isolated by using cDNA of pMCP. pMCP's cDNA was derived from RNA transcribed in porcine vascular endothelial cells. Namely, pMCP's promoter of the invention regulates expression of pMCP in the porcine vascular endothelial cells. Consequently, by using pMCP's promoter of the invention, genes of human complement inhibitors and those of such thrombosis-inhibiting factors as thrombomodulin can be expressed in the porcine organs, particularly the porcine vascular endothelial cells. Furthermore, by using pMCP's promoter of the invention, various structural genes can effectively, selectively and specifically be expressed in the porcine organs, particularly the porcine vascular endothelial cells.

On the other hand, the promoters derived from the human complement-inhibitor gene or viral genome, all of which had been employed in the previous studies, could neither selectively, specifically nor effectively express the human complement inhibitor in the porcine endothelial cells.

This invention was accomplished on the basis of such findings. The purpose of the invention was to provide DNA possessing an activity of pMCP's promoter.

DISCLOSURE OF THE INVENTION

This invention provides the base sequence defined by Sequence No. 1, DNA comprising a part of the base sequence, and DNA containing the sequence.

Another invention provides DNA with an approximately 4.1-, 2.4-, 1.7-,0.9-, 0.5-, 0.07- or 0.05-kb upstream sequence from the 3'end of the base sequence defined by Sequence No. 1; and DNA with the base sequence defined by Sequence No. 2.

These DNAs possess pMCP-promoter activities.

BRIEF DESCRIPTION OF THE FIGURES

FIG. 2 compares the promoter activities of the invention and hDAF.

THE BEST MODE FOR APPLYING THE INVENTION

Figure 1:
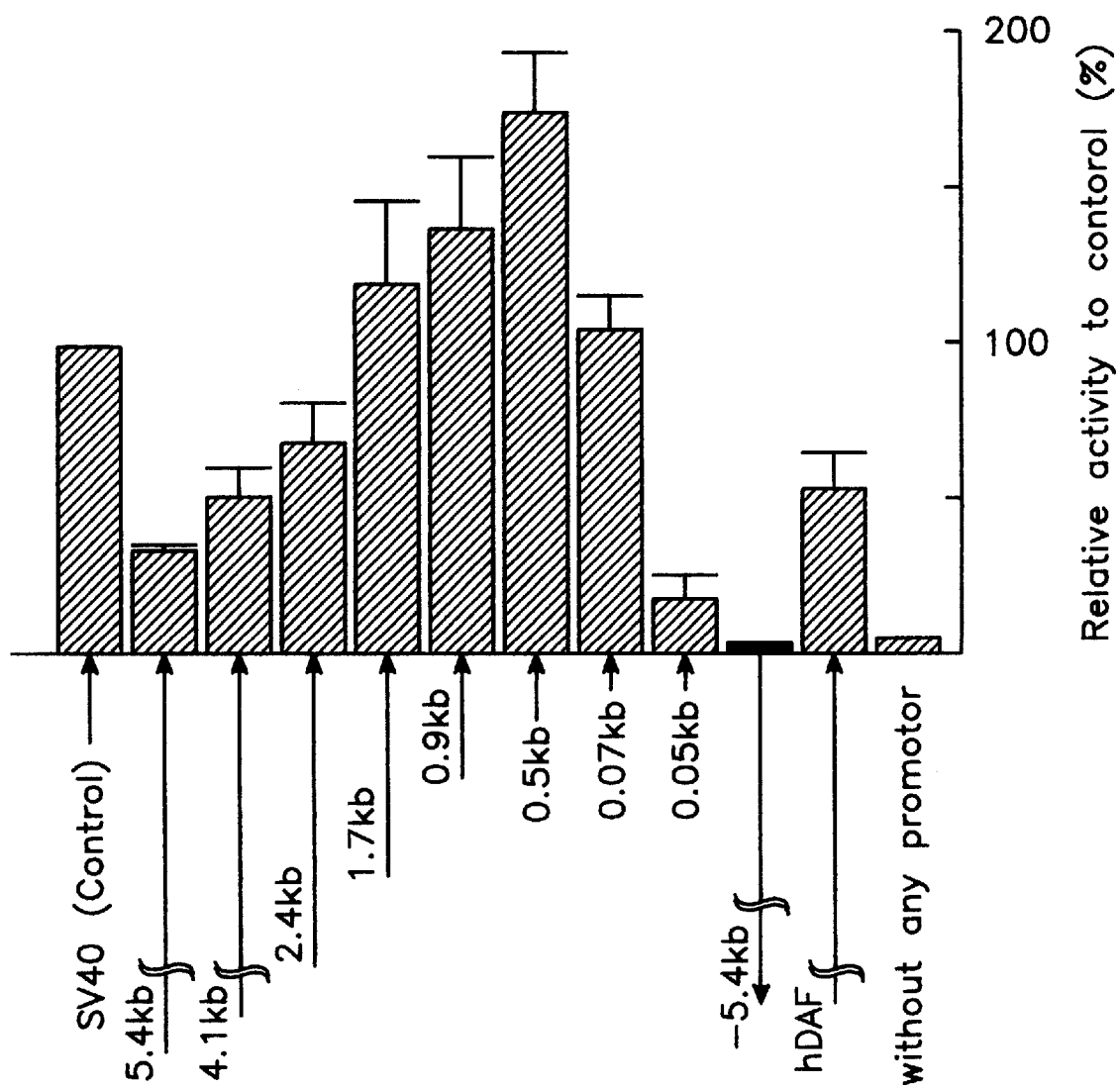
FIG. 1 shows the promoter activity of each promoter region.

The present invention is explained in detail in the following:

The base sequence of this invention defined by Sequence No. 1 is DNA with the promoter activity of pMCP. Such DNA can be obtained by preparing genomic DNA of the structural gene of pMCP from a commercially available porcine genomic library, identifying the promoter region existing on upstream region of genomic DNA, and digesting it with appropriate restriction enzymes.

With cDNA of pMCP or its parts as probes, genomic DNA of pMCP's structural gene can be cloned from porcine genomic library by the conventional plaque- or colony-hybridization method. By the plaque-hybridization method, plaques formed by phages containing the pMCP's genomic DNA are identified as follows: ① phages containing the porcine genomic library and *E. coli* are co-cultured on agar plates to make plaques; ② the plaques are transferred to nitrocellulose membrane filters, and then phage DNA in the plaques are fixed on the filters; and ③ the phage DNAs are hybridized with pMCP's probes labeled with radioisotope, and then autoradiographes of the filters are taken. By repeating such procedures, phages containing the pMCP's genomic DNA can be cloned.

To select the positive phage clones containing the promoter region of the genomic DNA, a region corresponding to the known first exon of human MCP cDNA can be excised from pMCP's cDNA and used as a probe to perform the plaque hybridization similarly as mentioned above, since the promoter gene of pMCP is believed to possess the first exon.

Thus, pMCP's genomic DNA containing the promoter region can be prepared from the cloned phage DNA.

The promoter region's DNA of pMCP can be prepared by digesting the upstream region of pMCP's genomic DNA with proper restriction enzymes, examining promoter activities of digested fragments, and collecting the fragments possessing the promoter activities.

The promoter activity can conventionally be examined: e.g., integrating the restriction enzyme-digested fragment into a vector for luciferase-activity determination, transfecting the vector into proper host cells, incubating the cells for a certain period, lysing the cells and then determining fluorescence of luciferase in the cell lysate.

The promoter region of pMCP's genomic DNA was thus obtained from the porcine genomic library. As shown in Examples described in the following, a promoter region comprising approximately 5,400 bp was obtained. By sequencing the region by a conventional method, the base sequence defined by Sequence No. 1 (5,418 bases) was identified.

By digesting the promoter region with proper restriction enzymes and examining the promoter activities of the resulting fragments by the above-described method, the approximately 1,700-bp upstream region proved to possess a high promoter activity. By sequencing the 1,700-bp region, the base sequence as defined by Sequence No. 2 (1,622 bp) was identified.

As shown in Examples, regions shorter and longer as well than the promoter defined by Sequence No. 2 were also found to possess the promoter activities. Consequently, so far as the activity of pMCP's promoter is retained, DNA of the present invention may consist of a part of the base sequence defined by Sequence No. 1 or DNA containing the base sequence defined by Sequence No. 1.

DNA of the present invention may be used as a promoter to express not only pMCP but also various other structural genes. In such cases, appropriate regions can be selected from the entire sequence, depending on the structural genes to express, host cell, and host animal.

The present invention's DNA thus obtained possesses the promoter activity to express the structural genes including pMCP and can be used for various purposes. As described above, DNA of the invention can favorably be integrated into the upstream part of human complement-inhibitor genes and used to generate a transgenic pig transformed with the human complement-inhibitor genes. Particularly, DNA of the invention can express the complement inhibitor on the porcine endothelial cells. Moreover, DNA of the invention can be used as the promoter to express other various structural genes than pMCP gene.

DNA of the present invention is not restricted to that prepared by the above-described method, but includes those prepared by other methods. As far as possessing substantially the same promoter activity, it will be validated if parts of the base sequence are deleted or replaced or inserted with one or more than two bases.

INDUSTRIAL APPLICABILITY

DNA of the present invention is the promoter gene of pMCP. In generating the transgenic pigs transformed with the human complement-inhibitor gene, the promoter gene can be integrated into the upstream part of the human complement-inhibitor genes. Since tissues and organs of such transgenic pigs do not cause hyperacute rejection, they can be transplanted to man. Consequently, the problem of the lack of donors for transplantation can effectively be solved.

EXAMPLES

The present invention will specifically be explained in detail with examples, but the scope of the invention is not restricted to these examples.

Example 1

A. Obtaining the Promoter Region of pMCP

① Cloning of a phage clone by hybridization

To obtain the genomic clones of PMCP, λ FIXII (Stratagene) and full-length pMCPcDNA (prepared by expression cloning and digestion of the expression vector with XhoI and NotI) were used for hybridization as the porcine genomic library and a probe, respectively. The plaque hybridization was carried out as follows:

First, two million clones of the above-described phage and an *E. coli* suspension were spread on 50 plates (totally 100 million clones). The phage clones formed plaques after overnight incubation at 37° C. To absorb the phages in the plaques, a sheet of nitrocellulose membrane filter for hybridization was placed on each plate for approximately 1 min.

After that, each filter was turned upside down and immersed in an alkaline denaturation solution (0.2 M NaOH, 1.5 M NaCl) to brake nuclei for 20 sec and then in a neutralizing solution [×2 SSC, 0.4 M Tris-HCl (pH 7.5)] for 20 sec. After drying, they were cross-linked under UV irradiation (GS Gene Linker, Bio Rad).

Second, these filters were blocked in a prehybridization buffer [50 % deionized formamide, ×4 SSC, 50 mM HEPES (pH 7), ×10 Denhardt solution, 100 mg/ml denatured salmon sperm DNA] for 4 h at 37° C.

The probe was labeled by treating pMCPcDNA with dNTP and Klenow (DNA polymerase I) in the presence of a radioisotope [$\alpha$-$^{32}$P] ATP. A radioisotope-labeled reverse chain was thus prepared with the cDNA as a template. The reverse chain can hybridize with the phage clone having the identical DNA sequences.

Then, the radio-labeled probe was placed on a gel-filtration column, spun down to remove the nonreacted and nonlabeled nucleotides, incubated for 3 min at 90° C., chilled on ice to maintain a single-chain form of DNA, and subjected to hybridization.

The prehybridized filters were placed in HybriPack and hybridized overnight at 37° C. with the above-described probe in the hybridization buffer.

Next, the filters were washed twice with SSC and SDS, allowed to react with the image-analyzer plates for 2 h at room temperature, and then analyzed with an image analyzer (Fuji Film Co.).

Finally, 30 positive clones were obtained. Gels of the positive clones were sucked with Pasteur pipettes and diluted with SM buffer. The clone-containing solution was thus prepared.

② The Secondary and Further Screening

The clone-containing solution was appropriately diluted and spread on plates (totally 30 plates). After that, hybridization was carried out again. Many positive plaques were observed on 20 plates. Twenty positive clones were thus obtained.

Such procedures were repeated three times. Finally, all of the clones were purified.

③ Classification of the Clones on the Basis of the Restriction-Enzyme Digestion Profiles To confirm whether the clones were independent, they were digested with a restriction enzyme EcoRI and then electrophoresed. The identical clones exhibit the same digestion profile. From various digestion profiles, 10 distinct clones were thus obtained.

④ Selection of the Phage Clones Containing the Promoter Region By Using the cDNA's Leading Region The phage clones containing the promoter region are believed to have the first exon. Consequently, a region supposedly corresponding to the first exon of human MCP was excised (SalI-SphI) from pMCPcDNA and subjected to hybridization as a probe. Four clones gave positive results.

⑤ Selection of the Promoter-Region Containing Phage Clones By Digestion With A Rare Restriction-Enzyme Site Four clones were digested with FspI, since its restriction-enzyme site scarcely exists in the first exon of pMCPcDNA. Only one clone was digested with the enzyme.

Consequently, it was found highly possible that this phage clone contained the promoter region.

⑥ Confirmation of the Promoter Region By Sequencing

The phage clone was digested with a combination of FspI and another restriction enzyme (EcoRI) to localize the FspI site of the first exon at the terminal of the digested fragment, integrated into a sequencing vector pBSIIKS+ (Stratagene) and sequenced (373 DNA Sequencer, Applied Biosystems, Inc.).

The result showed that the phage clone certainly contained the first exon.

From the restriction-enzyme digestion profile, it was proved that this phage clone contained the pMCP's promoter region, of which the full length was approximately 13 kb upstream the genome.

B. Determination of the Activity of pMCP's Promoter Region

① Preparation of A Construct For Assaying Promoter Activity

The promoter activity was determined with a system utilizing luciferase cDNA.

A 5.4-kb promoter region of pMCP bearing a T7 primer recognition site for sequencing (as the 13-kb DNA of the phage clone was too large to integrate, it was digested at the EcoRI sites) was digested with restriction enzymes BstEII and BssHII from the above-described sequencing plasmid. DNA sequence of the 5.4-kb promoter gene was conventionally determined as shown by Sequence No. 1 (5,418 bp).

The terminal of the above-described promoter region was blunted with T4 DNA polymerase and subcloned in the pGL-3 basic vector (Promega) for luciferase-activity determination at the SmaI sites. The vector for luciferase activity determination itself lacks a promoter gene, so it is useful to evaluate the promoter activity by integrating a to-be-tested promoter into the upstream part of the luciferase gene and determining luciferase activity. The luciferase activity can be determined by lysing transformed cells to prepare enzyme-containing lysate, allowing the lysate to react with a substrate of the enzyme and reading emitting fluorescence intensity.

② Preparation of Deletion Mutants

To obtain the promoter regions of various sizes, deletion mutants were prepared with a Kilosequence kit (Takara).

A series of pGL-3 vectors bearing promoters of 4.1-, 2.4-, 1.7-, 0.9-, 0.5-, 0.07- and 0.05-kb lengths were thus prepared.

Similarly, a pGL-3 vector bearing an SV40 promoter was prepared for control.

Furthermore, a vector bearing a reversed sequence of the above-described 5.4-kb promoter and that bearing human DAF (hDAF) promoter (approximately 4 kb) were also prepared for comparison.

③ Electroporation of the Plasmids Into Porcine Aorta Endothelial Cells

Luciferase activities were determined by using a porcine aorta endothelial cell line.

Cultured cells were detached with trypsin/EDTA solution, washed and suspended in HeBS buffer at a concentration of $3 \times 10^6$ cells/800$\mu$l.

A 800-$\mu$l portion of the cell suspension and a 15-$\mu$g portion of the above-described plasmids were transferred to a cuvette with 0.4-cm electrode clearance (a cuvette for cell electroporation) and electroporated with a Gene Pulser (Bio Rad) at 500$\mu$F and 300 V. The plasmids were integrated into the cells.

④ Determination of the Luciferase Activity

The above-described cells were cultured for 48 hours, collected, washed with PBS and treated with the cell-lysing solution for 10 min. Ten $\mu$l of the cell lysate was mixed with 50μl of the substrate of luciferase. Fluorescence of the reaction mixture was read with a Luminescence Reader (Aloka).

The results are shown in FIG. 1. The activities per $1\times10^5$ viable cells were calculated. Each column shows a relative activity, where the activity of a control pGL-3 vector bearing SV40 promoter is defined as 100. In FIG. 1, a symbol of −5.4 kb means a vector bearing a reversed fragment of about 5.4-kb promoter region. Similarly, that of hDAF means a vector bearing the hDAF promoter.

From the luciferase activities, the activities of the promoters ranging from approximately 0.07 to 1.7 kb were higher than that of the positive control, which was higher than hDAF promoter's activity (FIG. 1). Activities of the promoters of approximately 5.4-, 4.1-, 2.4- and 0.05-kb lengths were also noticed. The vector bearing the reversed fragment, however, showed no activity. From these results, it was evident that the above-described regions certainly possessed promoter activities.

Example 2
Sequencing the Promoter Region

DNA of an approximately 1.7-kb promoter region possessing a high activity as shown in FIG. 1 was sequenced.

With the T7 primer-recognition site which had been integrated into the upstream site of each deletion mutant, DNA was sequenced by the dye primer method. Sequencing was repeated twice. With regions difficult to identify, they were subcloned into pBSIIKS+ and sequenced by using the T3 primer recognition sites.

As a result, it was evident that the above-described approximately 1.7-kb promoter region possessed the DNA sequence as defined in Sequence No. 2 (1,622 bases).

Example 3
Determination of the Promoter Activity (Expression of the Human Complement Inhibitor)

① Transfection hDAFcDNA was connected to each of 5.4-kb (Sequence No. 1), 1.7-kb (Sequence No. 2) and 0.9-kb PMCP promoters or hDAF promoter. These genes were linearized, additionally ligated with a neomycin resistance gene as a selection marker and transfected into to $3\times10^6$ porcine cells by electroporation at 500μF and 300 V with a Gene Pulser (Bio Rad). The cells were cultured in a culture medium containing 250 μg/ml neomycin sulfate (Gibco). Colony-forming cells were collected. Expression of hDAF on the cell surface was analyzed with an FACScan (Becton Dickinson) after staining the cells with biotinylated anti-hDAF monoclonal antibodies (IA10,IIH6 and VIIIA7; Kinoshita, T., et al. (1985) J. Exp. Med. 162: 75) and PE-conjugated streptavidin.

② Assay for Complement Resistance

Some clones obtained by the above-described method were selected. Fifteen-thousand cells of each clone were allowed to react with antibodies and complement in a 96-well plate. As the antibodies, 100 μl of inactivated human serum was added to each well and allowed to stand for 30 min at 4° C. After washing with PBS, appropriately diluted normal human serum was added to each well as a complement source and allowed to stand for 3 h at 37° C. Surviving cells were determined with a WST-1 (Behringer Mannheim).

③ Results

1. Comparison of Expression with Various Promoters

A part of the results indicating relationship between each promoter and hDAF expression is shown in FIG. 2.

The horizontal axis of FIG. 2, FL2-H, represents the amount of hDAF expressed; it increases as the axis shifts rightwards. The vertical axis, count, represents cell number; it increases as the axis shifts upwards. Each peak shows the activity of a promoter indicated by the label. Black and blank peaks indicate FACScan responses obtained by cells reacted without and with anti-hDAF antibodies, respectively. As a result, no HGAF was expressed without the promoter. Comparing with hDAF promoter, any of pMCP promoters expressed hDAF effectively more than 20 times. Namely, it was confirmed that approximately 5.4-, 1.7- and 0.9-kb promoters effectively expressed the human complement inhibitor in the porcine endothelial cells.

2. Comparison of Resistance Against Complement By Various Promoters

No resistance was noticed in 50% human serum, if hDAF was expressed by the hDAF promoter; whereas, resistance of more than 80% was noticed even in 100% human serum, if hDAF was expressed by the pMCP promoters. Therefore, it was confirmed that hDAF exhibited its original function and resisted against the human complement, if hDAF was expressed on the porcine endothelial cells by the pMCP promoters.

What is claimed is:

1. An isolated DNA comprising SEQ ID NO:1 or isolated DNA comprising a part of the sequence, wherein said part has a size of at least 0.05 kb from the 3' end of the base sequence defined as SEQ ID NO:1.

2. Isolated DNA comprising 4.1, 2.4, 1.7, 0.9, 0.5, 0.07 or 0.05 kb from the 3' end of the base sequence defined as SEQ ID NO:1 as claimed in claim 1.

3. Isolated DNA comprising a base sequence defined as SEQ ID NO:2 as claimed in claim 1.

* * * * *

SEQUENCE LISTING

```
<160> NUMBER OF SEQ ID NOS: 2

<210> SEQ ID NO: 1
<211> LENGTH: 5418
<212> TYPE: DNA
<213> ORGANISM: Porcine sp.
<220> FEATURE:
<223> OTHER INFORMATION: n = g, c, a, or t

<400> SEQUENCE: 1
gaattctgcg tacacggggc cccggtggct ttacatcatc gctacagcga catgggatcc      60
gagccgtgtc tacaacctac acaacaacgc cagatcctta acccaatgca tgaggacagg     120
gctcaaacct gcggcctcat agatgctagt cagattcgtt tctgctgagc cacaatggga    180
actcctaatt ctagatcgat ctagaattag gagttcccat tgtggctcag cagaaacgaa    240
```

-continued

```
tctgactagc atctatgagg ccgcagtttg agccctgtcc tcatgcattg ggttaaggat    300
ctggcgttgt tgtgtaggtt gtagacacgg ctcggatccc atgtcgctgt agcgatgatg    360
taaagccacc ggggccccgt gctacgcaga attcntgcag cccgggggat ccactagttc    420
tagcnagaga gttgaaaatt taaagaacat ttctccccta atctcccaaa atatgggcaa    480
aggacaggta cccgtggcac tggaaaaata caggcaagca acccatgagt acatgaaaag    540
atgctccagg gttcggccta atggaagcct gaacaatgcc tatcacatcg tgggtttctg    600
aagaagtaac ttaaagaaac tagaaattaa atggctttct tagaatgaaa attctctatc    660
acaaggaaaa atgttgtatg ttgttttttcc cataatggag gtcagtgggc gctatgatta   720
acaaatatct gatgcctgtg acttttttaat tgcaagaaat ctgtgnagtt tttttattat   780
ctatgggaaa tattgcatat attaatgata tcacctaact tgtattattg agcaattctg    840
tccacatctg gcctttcatc tttcatctaa aaagcagggg ctggaccaac tgaccttcag    900
tgccattctt actgctaaca ttctaatttt gtttttattg cctttttgta caaaagtgtg    960
agagaagtca ttttaagtct gtgacattaa atgtaatttt ctgtctccag cattataata   1020
agaatcaaag atttaatcta atacaccgat ggaatattgt ttataacgta tttactgttt   1080
caagccttca aaaccaagag aaaacaaaat gagtacctgt tccttctgag aaatgccctt   1140
cttcctgttc agaatccctg tgtataacag gaatgctctc gagttaacag ccaagtaaga   1200
ggcccatcgg ctggcaggtg cccacctagc taggtgcaag cagaggtggc agtgctccca   1260
ggaccaacag cagaaacatg gcttaactat cctgtgttta gcagttctct tacgggtttt   1320
cacaacacct aaaagcgcc ctgatggggt aaagcctctg ccttcatgct gctgccccgt     1380
ctctgaaaag caggacgtaa atatacaatt taggaggtaa gagggacatc tgccattgtt    1440
ttctttaaca cagtcagcct ctgtttaatg aatcccagcc acctccctcc acctaccatc    1500
attcctaagg tttgcagagg agctgccata gagctcaaaa cacggwntac agacaagcat   1560
nttctccatc cctcctcatc ttctcacagg ccgcttgaca acatctctag gaggggggtgg  1620
aggcgccacc agtgttttgag cccctcgttc acgcaaagcc ttgactctgg agttctagtc  1680
ctcgcgggac cttaggaagt tcacggtcaa tactccgccc ttgggctcag acactaagag   1740
gatctccggg taaagagata gacagtagct ccatgcctga tttaggaaaa ctgtccgtac   1800
agacagttgt aattcattcc tttcagagac aaatcctgct ctcttcctag ttcctgaagt   1860
cattaaaatc aaaagctctc agaaacgtcc cagcatttgc taagtccacg ctgggggagg   1920
atgggcagag ccgtgttcag cgcgtttgac agcaacaccc acttatttca ttyagtatcc   1980
ataggcatat atcatgcacc tggtataggc ctctctctca gcactggaga tacagcaaga   2040
aaacgctatt cctgccccat ggagcttgtw maraaaata gannnaaaaa ccctttanaa     2100
anggaagctr ccngmtgggn cmaagtnaaa attaagtaaa aagaaawccg tgarraaacc    2160
cttcagtnat attaagaaag aaantagctt gatgaaaccc caggtgtana aattnncact    2220
aaaacaatgs tcccaattaa aaccccccmaa ttcatggaat ttactcnagt ancctgnaac   2280
taggraaacc aaattctagc cnatagtttc tcccttctaa atnttctcat gagaaaacaa    2340
yttatttcca aaganatttt ccatgatggg gaaagttttt ttcaactttg ctcaggtata    2400
aactgaanat acagcattaa agtaaagata gttgcagaga ccaccaaata gatacccgtt    2460
ttcanaaaaa gtgccaacat ggagccagag aacatttccg ttcatcacg cttttacggc     2520
tttgaaaatt aacagagatg ataatccccc mccttgggtt tccnactccn tccctcctna   2580
attttacctc ctttaattgt catcatgtct ggagattata atccaagata ctaagatgtt   2640
```

-continued

```
tatntcatac atcgcctcca cacagtgtgt ctnanaagct cttgcaagaa tccaaacatt   2700
gtgctggtct gggtagaaaa ggaaattcca tggtttgttg aacccaggaa ctcttcagta   2760
catctccgag gtaaaactgt ttaaatacaa ttaaagttct acagttaaag ggtaccctcc   2820
tccactgttg gtgggaatgt aaactggtac aatcactatg aaaaacagga tggaggtact   2880
tcagaaaatg aagtatagaa ctaccacagg atccagcact ctcactcctg ggcacctatc   2940
aggacaaaaa attcgctgca aaagatgcat gcacccatag ctatgttcac tgcagcagca   3000
ttcacaatag ccaagacatg gaaacgacct aaatgtccat caacagctga atgcattaag   3060
aagacgtggt atatacacac aatggaatac tactcaagtc atgaaaaaga acaaaagaat   3120
gccatttgca gcaacatggc atggctggaa ctagagactc atgctaaatg aagtcagtga   3180
gaaagagaaa gacaaatacc acatgatatc acttatatct ggaatctaat atacgacaca   3240
catgaaactt ccacagaaa  agaaaaccctn catggacttt ggagaacaga cttgtggttt   3300
csccaagggg ggargggggg aagaccgtgg gaggactggg gagctttggg gttaatagat   3360
gcaaaactat tgcctttnga atggataagc caatgggatc ctgctgtacc agaaccrggg   3420
aactatanct agtcacttgc kntagaacat gatggaggat natntgagan aaagaatatn   3480
tgtgtgtgtk agagagagag agactggctc cactttgctg tatagtagaa aactgacaga   3540
acaccgtaaa ccattaaata aaatccagt  aaaaatttaa aaataaaaac acacattggt   3600
tccaatgtgt ttaaaagcaa taaagttcta taattgcagc agatgcatct gaggtttaca   3660
cggagagctt ccattcctta ccatcctctc attccttaac tctaatgtga tacaggttct   3720
attctcacca ttctatgaac aaaagagcag ctgatttaca ggttggattt ttcaaaaaaa   3780
aaaatttctt taccaggatc ccaaatgtaa caaagggtca atatagaaaa cttaaaaagc   3840
acagccaaag agaaatatac ataagccttt caactattaa ttttgattaa tatccaacga   3900 atctctttt  aagtgtatca atatattatt cattttaata aaagaaattg caagaggcac   3960 ttgcttttc  tgcttacaaa tacgttttct caaatcgatt ttttttatat actgtttgca   4020
tagaatttca atccataaag ctacctattg aaaattcctt atatttctgc taaacactta   4080
agggcttata ttttctccaa atttatacat ccttgctcac agttctgacg atgtctttgg   4140
gataaactct aaatggaact agaggtttaa aagttatgtc catttaaaac ttttaacaca   4200
aaaaaaggta agttaaaaag taaagttttg gggaggctgc tggtcgcccc ccaacattg   4260 gctgacattt ttattctttg acaacaaata ggaagaaaat gtcaatgtct ttttttactg   4320
cttaatactg gtcatgttac ttttctttcc ttttgctaat catacaggct tactcacaac   4380
tctacaaaaa aatcttactc attcctaatg ttccttcatt gagagattgg tttgccggaa   4440
acgttctcac tctcaccaag tcccaacagt cccaactcta acgacggtcg ctgcttccag   4500
aaatacggca cttaaggcac cctcgtcctt acctttttca tgcatgtgta tttcattttc   4560
aataaaacat tgagttgttc caaggccaga ccatagagtt gagccccaac atgctagtgg   4620
cccagtgtga tgtaataatt taccttccca gggtcctct  ccggggggt  acaggcgaga   4680 ctaagtgact ttaagctgtt gggagaacaa tggccaaacc tttcgtgatt ttgaaatcta   4740
tcaggccacg agacacttcg gtagcggacg ctcaaccctg gaatcccaa  ctattgtccc   4800 aaattttgcc tgactcgtgc caaagattga gccagggccc gggtgtccag gcagtctgca   4860 gtgcccagt  ccccaccaga gccctgaagg gtgtcgggcc ccacgaaacc gctgcccggg   4920
ctctagggtt tctgttttca ggtcgctgcg ctttattctc taattcagcg ttcccgaaag   4980
```

-continued

| | |
|---|---|
| agaccatgag gacccgccca gtgtccttta caccttcccg tgtcgggtgg cgacagctgt | 5040 |
| ttacgaagaa gagtgcacca cccttcccg caagccgcag cggttagttc cgcagaagga | 5100 |
| ggagccaggg cgtcgggccg cagctggag agaggcccgg cagcgggcgc cgcggagcag | 5160 |
| caagggcgtc cctctctcgg ccggagcccc gccccgcccc gccccacgg cccgccttg | 5220 |
| cggcccgccc attggctccg ccgggccctg gagtcactcc ctagagccac ttccgcccag | 5280 |
| ggcggggccc aggccacgcc cactggcctg accgcgcggg aggctcccgg agaccgtgga | 5340 |
| ttcttactcc tgctgtcgga actcgaagag gtctccgcta ggctggtgtc gggttacctg | 5400 |
| ctcatcttcc cgaaaatg | 5418 |

<210> SEQ ID NO: 2
<211> LENGTH: 1622
<212> TYPE: DNA
<213> ORGANISM: Porcine sp.

<400> SEQUENCE: 2

| | |
|---|---|
| gatcccaaat gtaacaaagg gtcaatatag aaaacttaaa aagcacagcc aaagagaaat | 60 |
| atacataagc ctttcaacta ttaattttga ttaatatcca acgaatctct ttttaagtgt | 120 |
| atcaatatat tattcatttt aataaaagaa attgcaagag gcacttgctt tttctgctta | 180 |
| caaatacggt ttctcaaatc gatttttttt atatactgtt tgcatagaat ttcaatccat | 240 |
| aaagctacct attgaaaatt ccttatattt ctgctaaaca cttaagggct tatatttct | 300 |
| ccaaatttat acatccttgc tcacagttct gacgatgtct ttgggataaa ctctaaatgg | 360 |
| aactagaggt ttaaaagtta tgtccattta aaacttttaa cacaaaaaaa ggtaagttaa | 420 |
| aaagtaaaag tttggggagg ctgctggtcg ccccccaac attggctgac attttttattc | 480 |
| tttgacaaca aataggaaga aaatgtcaat gtctttttt actgcttaat actggtcatg | 540 |
| ttactttttct ttccttttgc taatcataca ggcttactca caactctaca aaaaaatctt | 600 |
| actcattcct aatgttcctt cattgagaga ttggtttgcc ggaaacgttc tcactctcac | 660 |
| caagtcccaa cagtcccaac tctaacgacg gtcgctgctt ccagaaatac ggcacttaag | 720 |
| gcaccctcgt ccttaccttt ttcatgcatg tgtatttcat tttcaataaa acattgagtt | 780 |
| gttccaaggc cagaccatag agttgagccc caacatgcta gtggcccagt gtgatgtaat | 840 |
| aatttacctt cccaggggtc ctctccgggg gggtacaggc gagactaagt gacttttaagc | 900 |
| tgttgggaga acaatggcca aacctttcgt gattttgaaa tctatcaggc cacgagacac | 960 |
| ttcggtagcg gacgctcaac cctgggaatc ccaactattg tcccaaattt tgcctgactc | 1020 |
| gtgccaaaga ttgagccagg gcccgggtgt ccagcagtc tgcagtgccc cagtccccac | 1080 |
| cagagccctg aagggtgtcg ggcccacga aaccgctgcc cgggctctag ggtttctgtt | 1140 |
| ttcaggtcgc tgcgctttat tctctaattc agcgttcccg aaagagacca tgaggacccg | 1200 |
| cccagtgtcc tttacacctt cccgtgtcgg gtggcgacag ctgtttacga agaagagtgc | 1260 |
| accacccttt cccgcaagcc gcagcggtta gttccgcaga aggaggagcc agggcgtcgg | 1320 |
| gccgcagctg ggagagaggc ccggcagcgg gcgccgcgga gcagcaaggg cgtccctctc | 1380 |
| tcggccggag ccccgccccg ccccgccccc acggcccgc cttgcggccc gccattggc | 1440 |

-continued

```
tccgccgggc cctggagtca ctccctagag ccacttccgc ccagggcggg gcccaggcca    1500
cgcccactgg cctgaccgcg cgggaggctc ccggagaccg tggattctta ctcctgctgt    1560
cggaactcga agaggtctcc gctaggctgg tgtcgggtta cctgctcatc ttcccgaaaa    1620
tg                                                                   1622
```